US008225668B2

(12) United States Patent
Yabushita et al.

(10) Patent No.: US 8,225,668 B2
(45) Date of Patent: Jul. 24, 2012

(54) ULTRASONIC WAVE TESTING METHOD AND ULTRASONIC TESTING DEVICE USING THIS METHOD

(75) Inventors: Hideki Yabushita, Chiba (JP); Tatsuyuki Nagai, Osaka (JP); Shigeyuki Matsubara, Osaka (JP); Norio Nemoto, Ibaraki (JP); Hiroshi Miyamoto, Chiba (JP)

(73) Assignees: Independent Administrative Institution Japan Aerospace Exploration Agency, Tokyo (JP); Non-Destructive Inspection Company Limited, Osaka (JP)

( * ) Notice: Subject to any disclaimer, the term of this patent is extended or adjusted under 35 U.S.C. 154(b) by 821 days.

(21) Appl. No.: 11/988,304

(22) PCT Filed: Jun. 30, 2006

(86) PCT No.: PCT/JP2006/313117
§ 371 (c)(1),
(2), (4) Date: Jul. 25, 2008

(87) PCT Pub. No.: WO2007/004571
PCT Pub. Date: Jan. 11, 2007

(65) Prior Publication Data
US 2009/0165561 A1 Jul. 2, 2009

(30) Foreign Application Priority Data
Jul. 4, 2005 (JP) ................... 2005-195598

(51) Int. Cl.
*G01N 29/26* (2006.01)
(52) U.S. Cl. ............... 73/624; 73/625; 73/628
(58) Field of Classification Search .......... 73/624, 73/634, 621, 628, 625, 626
See application file for complete search history.

(56) References Cited

U.S. PATENT DOCUMENTS
3,165,922 A * 1/1965 Worlton .................. 73/627
(Continued)

FOREIGN PATENT DOCUMENTS
JP 58-178252 A 10/1983
(Continued)

OTHER PUBLICATIONS
International Search Report mailed on Sep. 26, 2006.
(Continued)

*Primary Examiner* — Hezron E Williams
*Assistant Examiner* — Rose M Miller
(74) *Attorney, Agent, or Firm* — Rader, Fishman & Grauer PLLC (57) ABSTRACT

An ultrasonic wave propagating method capable of propagating plate waves between a probe and a test piece despite variations in the thickness or the surface angle of a test piece, and an ultrasonic propagating device and an ultrasonic testing device using this method. Ultrasonic waves are propagated between a probe (20) for transmitting or receiving ultrasonic waves and a test piece (100) for propagating plate waves. When propagating ultrasonic waves, a probe that can set an ultrasonic wave incident angle from the probe (20) to the test piece (100) and/or an ultrasonic wave receivable angle from the test piece to the probe in a plurality of states is used. A focal point type probe may be used as the above probe (20). When this type of a probe is used, it is oriented such that an oscillating direction axis L1 in the direction of which a reference axis along the propagation route of ultrasonic waves is oscillated around the focal point of the probe crosses the propagation element surface L2 including the test piece surface of a ultrasonic wave propagation element.

10 Claims, 6 Drawing Sheets

U.S. PATENT DOCUMENTS

| | | | | |
|---|---|---|---|---|
| 3,512,400 | A | * | 5/1970 | Lynnworth ................ 73/597 |
| 4,674,334 | A | * | 6/1987 | Chimenti et al. ........... 73/627 |
| H924 | H | * | 6/1991 | Chimenti .................. 73/644 |
| 6,092,421 | A | * | 7/2000 | Bar-Cohen et al. ......... 73/624 |

FOREIGN PATENT DOCUMENTS

| | | |
|---|---|---|
| JP | 61-256255 A | 11/1986 |
| JP | 62-209356 A | 9/1987 |
| JP | 02-45454 U | 3/1990 |
| JP | 02-13973 Y2 | 4/1990 |
| JP | 04-256852 A | 9/1992 |
| JP | 05-168094 A | 7/1993 |
| JP | 10-239286 A | 9/1998 |
| JP | 11-064309 A | 3/1999 |
| JP | 11-118711 A | 4/1999 |
| JP | 2001-221784 A | 8/2001 |
| JP | 2004-340809 A | 12/2004 |
| JP | 2005-055197 A | 3/2005 |
| JP | 2005055197 A * | 3/2005 |
| JP | 2005-134192 A | 5/2005 |
| JP | 2005134192 A * | 5/2005 |

OTHER PUBLICATIONS

International Preliminary Report (International Application No. PCT/JP2006/313117) mailed on Apr. 24, 2008.

Shigeyuki Matsubara et al., "Air-Coupled Ultrasonic Inspection Method for CFRP (2nd Report)", *FY2003 Non-Destructive Inspection Co., Ltd., Fall Convention Lecture Summaries*, pp. 3-4 (2003).

Akio Jitsumori, "Signal Processing on Industrial Ultrasonic Sensing—Generation and Detection of Lamb Wave Using Linear Array Transducer and Its Application for Flaw Detection", *Recent Developments in Sensing and Signal Processing Technologies*, pp. 9-15 (Nov. 12, 1997).

* cited by examiner

ULTRASONIC WAVE TESTING METHOD AND ULTRASONIC TESTING DEVICE USING THIS METHOD

FIELD OF THE INVENTION

The present invention relates to an ultrasonic wave testing method for propagating an ultrasonic wave between a probe which transmits and receives the ultrasonic wave and a test piece through which its generation plate wave is propagated thus to examine the test piece and to an ultrasonic testing device using the method.

BACKGROUND OF THE INVENTION

Figure 8:
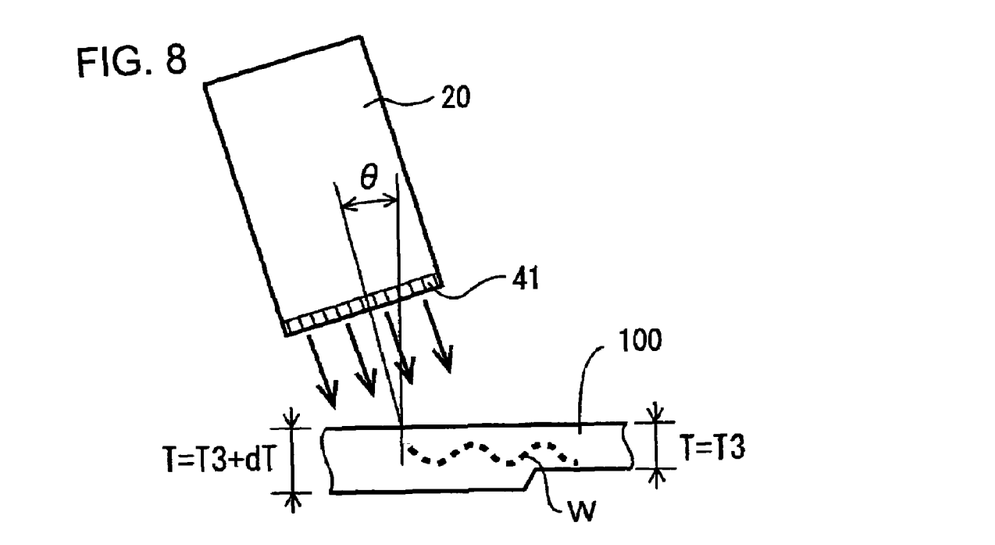
FIG. 8 is a partially cross sectional view of a transmitter in a conventional ultrasonic testing device.

Such a test method with an ultrasonic wave propagated through the air as shown in FIG. 8 is known where the ultrasonic wave is propagated from a probe to a test piece which in turn generates a plate wave and allows the probe to measure the plate wave generated in the test piece (See Patent Document 1).

Another test method is also disclosed in Non-patent Document 1 for improving the intensity of transmission and reception of incident/leak signals with the use of a probe which is curved along the horizontal direction.

Patent Document 1: Japanese Patent Laid-open Publication No. 2005-055197.

Non-Patent Document 1: "Air-coupled ultrasonic inspection method for CFRP (2nd report)" by Shigeyuki Matsubara et al, The Japanese Society for Non-Destructive Inspection, Autumn Proceedings in Heisei 15, pp. 3-4.

In common, the probe employed in a test of this type is arranged for transmitting and receiving an ultrasonic wave along one direction. Accordingly, during the propagation of the ultrasonic wave from the probe, the ultrasonic wave propagating from the probe falls at a uniform degree of the incident angle θ on the test piece.

Figure 9:
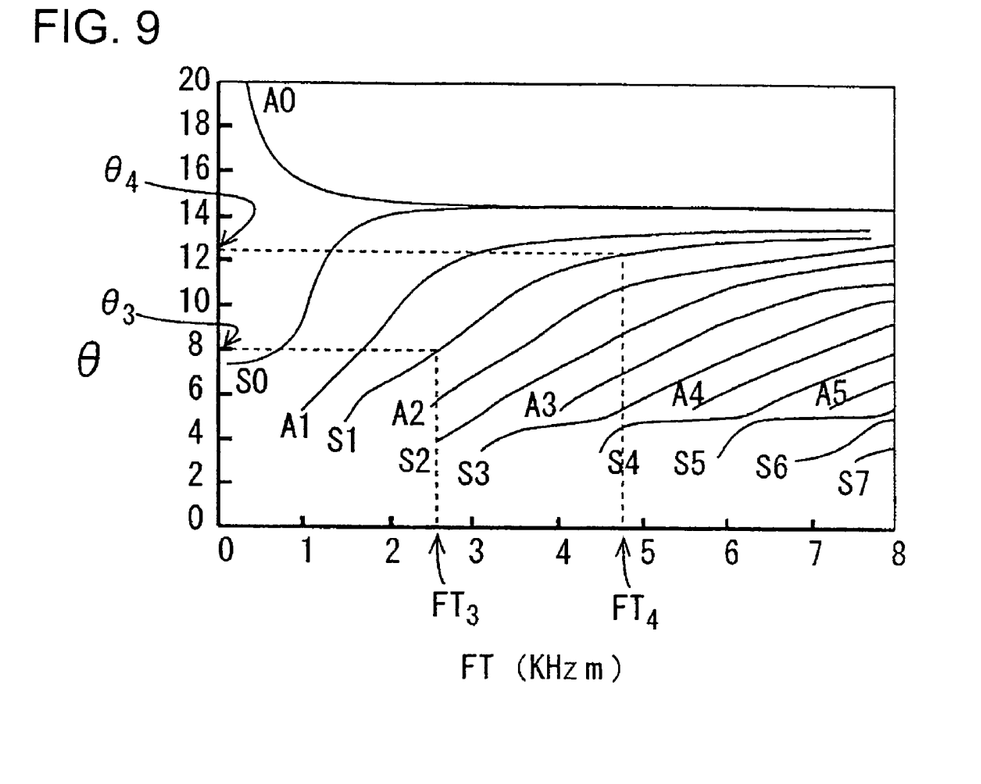
FIG. 9 is a schematic view, similar to FIG. 4, of the conventional ultrasonic testing device.

And now, FIGS. 8 and 9 illustrate the relationship between the product FT (kHz·m) of the frequency of the plate wave and the thickness of the test piece and the incident angle θ(°) at which the ultrasonic wave is directed to generate a plate wave, at different modes of the plate wave denoted by A0 to A5 and S0 to S7. Accordingly, for example, to match the product FT3 at the mode S1 where the frequency of the plate wave is F and the thickness of the test piece is T3, the incident angle of θ3 is desired and, in practice, set up with the use of a proper jig.

However, when the thickness at the incident point is changed from T=T3 which has been predicted to T=T3+dT=T4, the incident angle turns up to θ=θ4 which disallows the ultrasonic wave to penetrate the test piece for generating a plate wave. Also, when the incident angle θ is relatively changed by the effect of undulations of the surface of the test piece, it disallows the ultrasonic wave to penetrate the test piece for generating a plate wave with the same reason. The relationship between the two factors depends largely on the material properties of the test piece. Accordingly, the probe has to be reset every time when the test piece is changed in the thickness or the material properties. Moreover, any change in the condition of the material properties may inhibit the ultrasonic testing action itself from being conducted.

SUMMARY OF THE INVENTION

It is hence an object of the present invention, in view of the foregoing aspects, to provide an ultrasonic wave testing method which is capable of propagating a plate wave between a probe and a test piece regardless of variations in the thickness or the angle at the surface of the test piece and provide an ultrasonic testing device using the method.

For achievement of the object, an ultrasonic wave propagating method according to the present invention is provided for propagating an ultrasonic wave between a probe for transmission and reception of the ultrasonic wave and a test piece through which its generating plate wave is propagated thus to examine the test piece, characterized in that the probe is arranged of a focusing type for simultaneously providing different degrees of the incident angle at which the ultrasonic wave is directed from the probe to the test piece and/or the receivable angle at which the ultrasonic wave from the test piece is received by the probe and oriented so that the direction of its rocking movement along which the reference axis aligned with the propagating path of the ultrasonic wave is turned from one side to the other on the focal point of the probe extends to intersect the surface of propagation of the ultrasonic wave including the outer surface of the test piece, and the plate wave of a specific mode is generated by the ultrasonic wave emitted from the probe and received by the test piece at the incident angle which is determined depending on the property of the test piece as it corresponds to the product of the frequency of the ultrasonic wave at the incident location and the thickness of the test piece, propagated through the test piece, released from the test piece at the output angle which is determined depending on the property of the test piece as it corresponds to the product of the frequency of the ultrasonic wave at the output location and the thickness of the test piece, and received by the probe.

Figure 2:
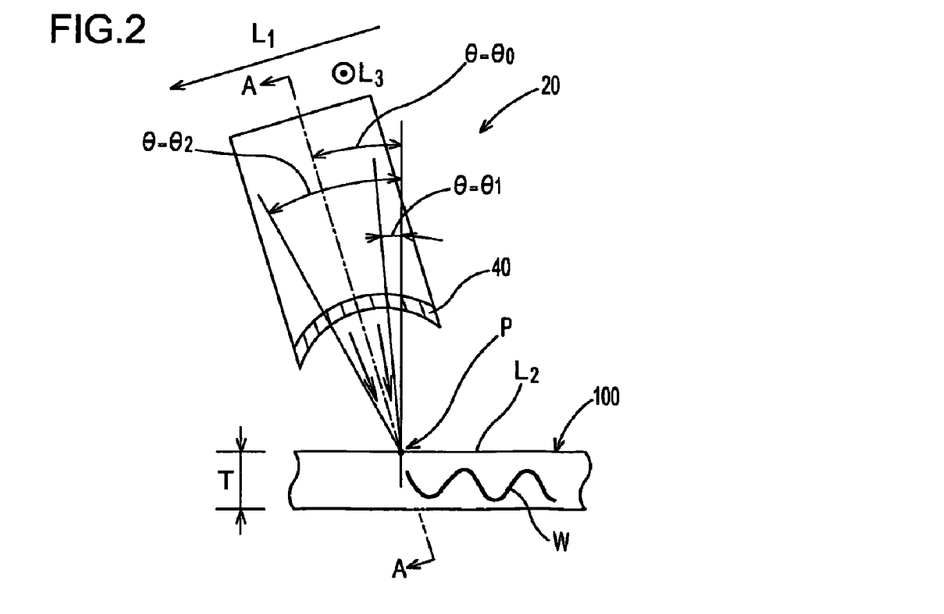
FIG. 2 is a partially cross sectional view of a transmitter shown in FIG. 1.
Figure 4:
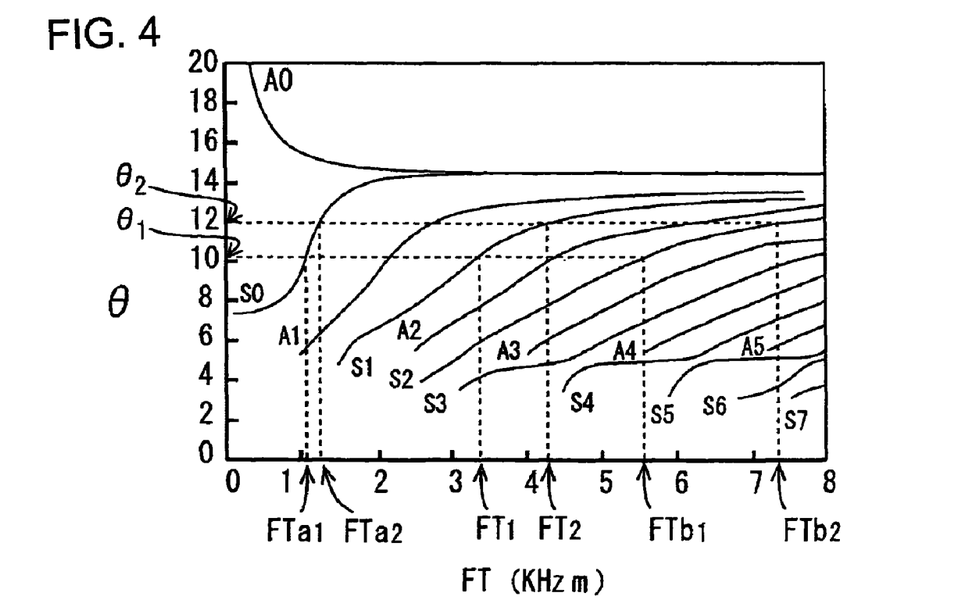
FIG. 4 is a graphic diagram showing the relationship between the product FT of the frequency F of an ultrasonic wave and the thickness T of a test piece and the incident angle θ at different modes (denoted by A0 to A5 and S0 to S7) of a plate wave.

When the probe of a focusing type is employed of which the oscillator is curved, for example, as shown in FIG. 2, the direction L1 (a direction of rocking movement on the focal point P of the probe of the reference axis Q aligned with the propagating path of the ultrasonic wave is set to intersect the surface of propagation L2 including the outer surface of the test piece 100 about the focal point P. This allows the incident angle θ (as well as the receivable angle) of the ultrasonic wave to be varied from the reference angle θ=θ0 to different angles, as denoted by the arrows in FIG. 2. Accordingly, the ultrasonic wave falling at a desired degree, between θ1 and θ2, of the incident angle θ can be propagated depending on the product, FT1 to FT2, of frequency and thickness, as shown in FIG. 4.

Also as apparent from FIG. 2, the focal point P of the probe may be located on and about the outer surface of the test piece 100. This clarifies the coordinates at the incident point of the ultrasonic wave. It is not mandatory that the focal point P is located on the surface of the test piece.

Figures 3A, 3B:
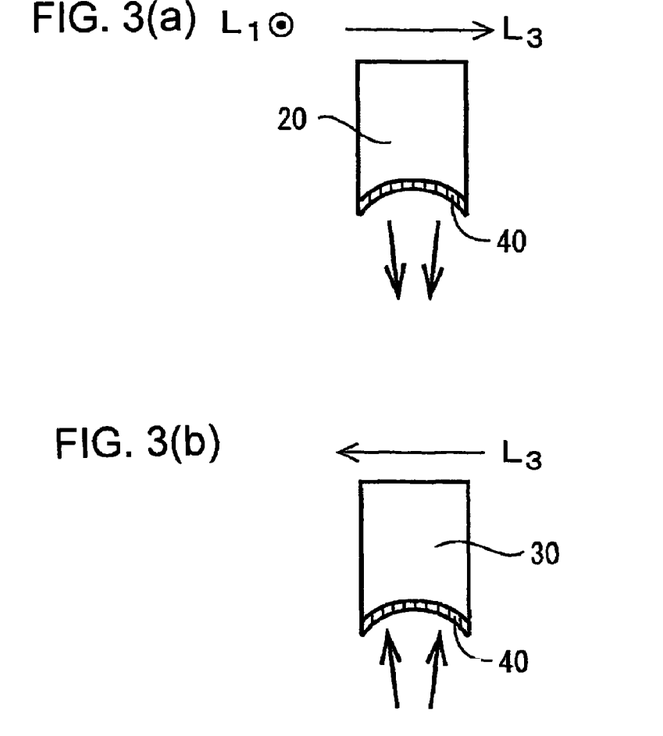
FIG. 3(a) is a cross sectional view taken along the line A-A of FIG. 2.
FIG. 3(b) is a cross sectional view of a receiver similar to FIG. 3(a)

Alternatively, as shown in FIGS. 2 and 3, the probe may be arranged oriented so that the direction L3 of second rocking movement orthogonal to the direction L1 of the rocking movement extends in parallel with the surface of propagation of the ultrasonic wave including the outer surface of the test piece. This allows the ultrasonic wave to be not dispersed but converged on the test piece 100, hence increasing the intensity at both the transmission end and the reception end.

Alternatively, an ultrasonic testing device according to the present invention is provided for propagating an ultrasonic wave between a probe for transmission and reception of the ultrasonic wave and a test piece through which its generating plate wave is propagated thus to examine the test piece characterized in that the probe is arranged of a focusing type for simultaneously providing different degrees of the incident angle at which the ultrasonic wave is directed from the probe to the test piece and/or the receivable angle at which the ultrasonic wave from the test piece is received by the probe and oriented so that the direction of its rocking movement along which the reference axis aligned with the propagating path of the ultrasonic wave is turned from one side to the other on the focal point of the probe extends to intersect the surface of propagation of the ultrasonic wave including the outer surface of the test piece, and the plate wave of a specific mode is generated by the ultrasonic wave emitted from the probe and received by the test piece at the incident angle which is determined depending on the property of the test piece as it corresponds to the product of the frequency of the ultrasonic wave at the incident location and the thickness of the test piece, propagated through the test piece, released from the test piece at the output angle which is determined depending on the property of the test piece as it corresponds to the product of the frequency of the ultrasonic wave at the output location and the thickness of the test piece, and received by the probe.

In the ultrasonic wave testing method and the ultrasonic testing device using the method, both the incident angle or the receivable angle of the propagation of the ultrasonic wave and the product of the frequency of the ultrasonic wave and the thickness of a test piece are increased thus to improve the propagation of the ultrasonic wave regardless of the thickness, the surface undulation, and the material properties of the test piece.

Other objects, arrangements, and advantages of the present invention will be apparent from the description of the embodiments of the present invention.

DESCRIPTION OF NUMERALS AND SYMBOLS

1: ultrasonic testing device, 2: PC, 3: plate wave transducer, 4: preamplifier, 5: filter, 6: A/D converter, 7: scanner driver, 8: scanner, 10: scan head, 20: transmitter, 30: receiver, 40: oscillator (of concave type), 41: planer oscillator, 42: sensor array oscillator, 43: concave type acoustic lens, 44: convex type acoustic lens, 45: oscillator (of convex type), 100: test piece (CFRP), 100a, 100b: different test piece materials, W: plate wave, L1: direction of first movement, L2: surface of propagation, L3: direction of second movement, P: focal point, θ: incident angle, F: frequency, T: thickness, D: direction of scanning.

BEST MODES FOR EMBODYING THE INVENTION

Figure 1:
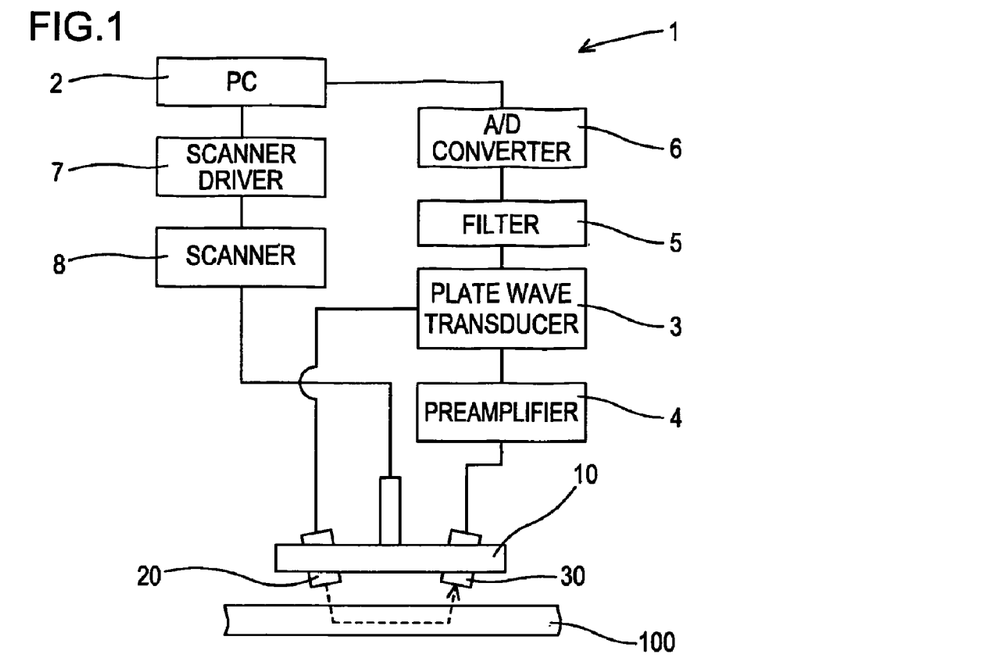
FIG. 1 is a schematic view of an ultrasonic testing device according to the present invention.

The present invention will be described in more detail, referring to the accompanied drawings. FIG. 1 illustrates an ultrasonic testing device 1 according to the present invention. The ultrasonic testing device 1 is arranged for transmitting an ultrasonic wave from a transmitter 20 in a scan head 10 with the use of a plate wave transducer 3 which is controlled by a personal computer 2 (referred to as a PC hereinafter) and receiving at a receiver 30 the returning of the ultrasonic wave which is then transferred via a pre-amplifier 4, a filter 5, and an A/D converter 6 to the PC 2 where it is subjected to arithmetic operations. The PC 2 is also provided for starting the action of a scanner 8 through a scanner driver 7 to inspect any flaw in a test piece 100 with a scan head 10.

Figure 7A:
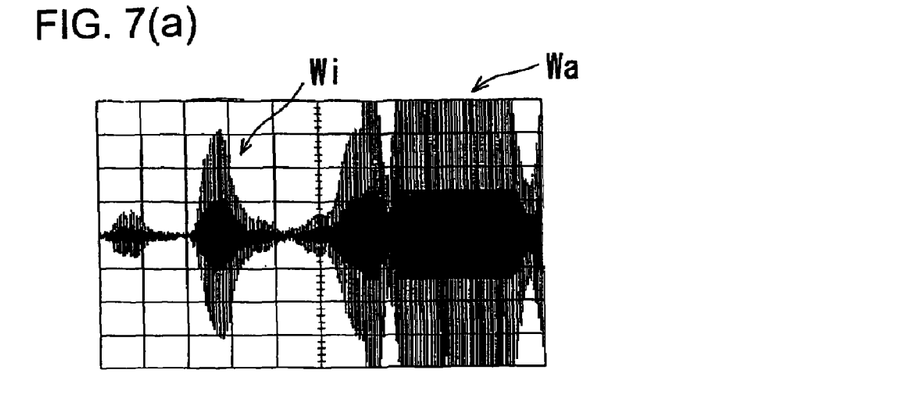
FIGS. 7(a) and 7(b) are profiles of the received signal according to the present invention, 7(a) showing a normal region and 7(b) showing a peel defective region respectively of the test piece.
Figure 7B:
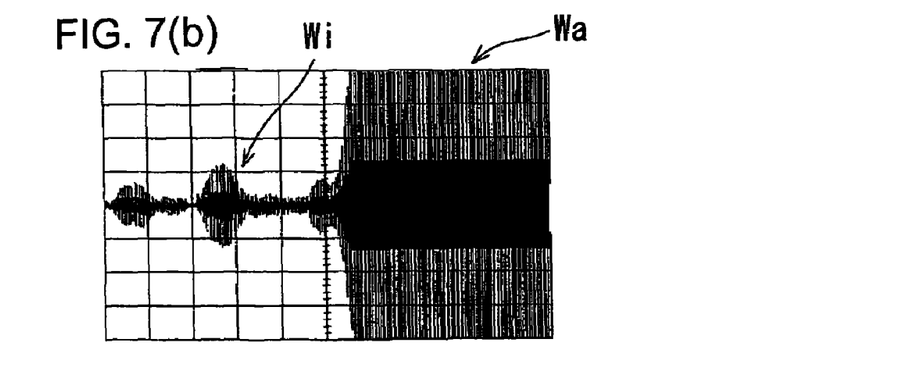

It is noted that the test piece 100 in this embodiment is a carbon fiber reinforced plastic (CFRP) material. As shown in FIG. 7, the received signal consists mainly of a test piece propagated wave Wi which is higher in the sonic speed and thus received earlier and an air propagated wave Wa which is delayed. The test piece propagated wave Wi in the received signal shown in FIG. 7(b) is decayed at the peel defects as comparing with the fully normal wave shown in FIG. 7(a).

FIG. 2 is a partially enlarged view of the transmitter 20. As shown in FIG. 2, the transmitter 20 is implemented by a focusing type probe of which the oscillator 40 is curved. The curved surface of the oscillator 40 is shaped to an arcuate plane in three dimensions, such as a spherical plane, an oval arcuate rotation plane, or a polygonal plane, of which one curving direction L1 (a first direction of rocking movement of the propagating path of the ultrasonic wave) intersects the surface of propagation L2 which includes the outer surface of the test piece 100 about the focal point P. Although not shown, the first direction of rocking movement L1 at the receiver 30 is also arranged to intersect the surface of propagation L2.

FIG. 3(a) is a cross sectional view of the transmitter 20 taken along the A-A line while FIG. 3(b) is a cross sectional view of the receiver 30 along the A-A line. As apparent from FIGS. 3(a) and 3(b), the oscillators 40 of both the transmitter 20 and the receiver 30 in this embodiment are oriented so that the other direction L3 (a second direction of rocking movement on the focal point P) of their curved surface which is set at a right angle to the first axis L1 extends in parallel with the surface of propagation L2 of the ultrasonic wave which includes the outer surface of the test piece 100 while the first direction of rocking movement L1 along which the reference axis Q aligned with the propagating path of the ultrasonic wave is turned from side to side on the focal point P of the probe is intended to intersect the surface of propagation L2.

FIG. 4 is a graphic diagram showing the relationship between the product FT of the frequency F of the ultrasonic wave and the thickness T of the test piece and the incident angle θ at each mode (denoted by A0 to A5 and S0 to S7) of the plate wave depending on the material properties of the test piece 100. When the relationship is satisfied, a particular mode of the plate wave develops. According to the present invention, with the oscillators 40 of both the transmitter 20 and the receiver 30 implemented by a surface curved shape of focusing type probe, the first direction of rocking movement L1 is intended to intersect the surface of propagation L2. This allows the incident angle θ (as well as the receivable angle) of the ultrasonic wave to be varied from the reference (θ=θ0) to any of different angles (between θ1 and θ2) as denoted by the arrows in FIG. 2.

As the result, as shown in FIG. 4 the ultrasonic wave falling at a desired degree, between θ1 and θ2, of the incident angle θ can be propagated as a plate wave W of the mode S1, for example, depending on the product, FT1 to FT2, of frequency and thickness. More particularly, the ultrasonic wave falling at the incident angle between θ1 and θ2 can be propagated at the mode S0 when the product of frequency and thickness ranges from FTa1 to FTa2 or at the mode S2 when the same ranges from FTb1 to FTb2. Also, two or more modes of the plate wave can be generated simultaneously in the test pieces 100 by the relationship of each ranges between the incident angle θ and the product of frequency and thickness FT. In addition, since the oscillators 40 of both the transmitter 20 and the receiver 30 are oriented so that their second direction of movement L3 extends in parallel with the surface of propagation L2, the ultrasonic wave can be not dispersed but focused at the focal point P on the test piece 100 thus to increase its intensity at both the transmission end and the reception end.

Figure 5A:
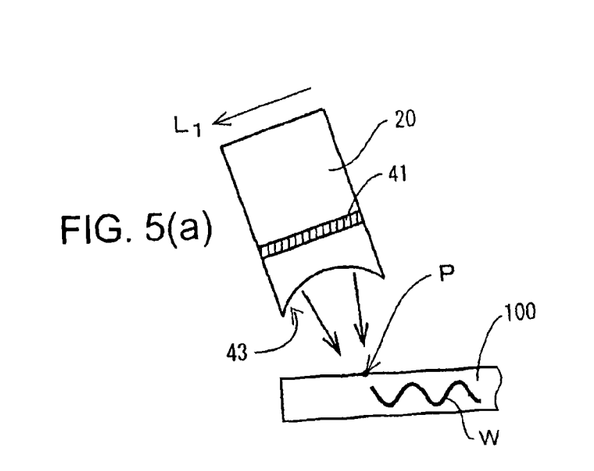
FIGS. 5(a) to 5(d) are views, similar to FIG. 2, showing modifications of the transmitter according to the present invention.

The transmitter 20 is not limited to the arrangement of the focusing type probe illustrated. For example, a plat oscillator 41 may be employed as accompanied with a concave type acoustic lens 43 mounted to the emission surface of the transmitter 20, thus forming a focusing type probe as shown in FIG. 5(a).

Figure 5B:
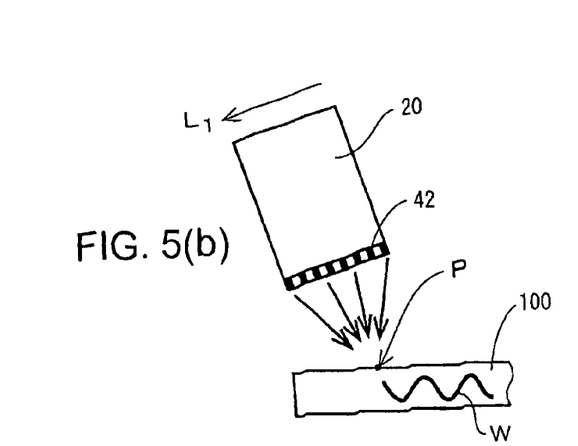

Alternatively, a sensor array oscillator 42 may be employed as shown in FIG. 5(b). This comprises a linear (or area) array of oscillators which oscillate in a sequence of time to focus the ultrasonic wave at the focal point P on the test piece 100.

Figure 5C:
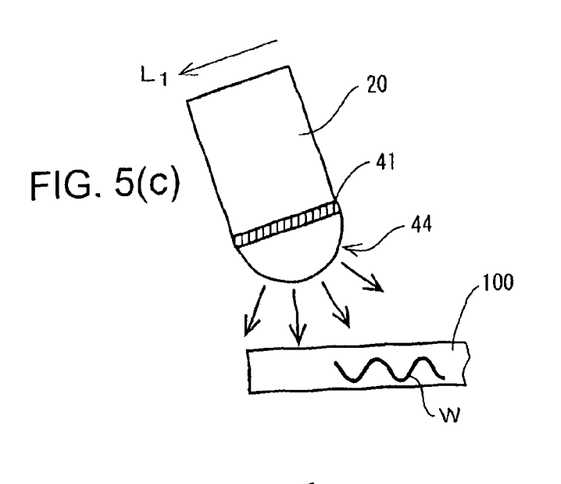
Figure 5D:
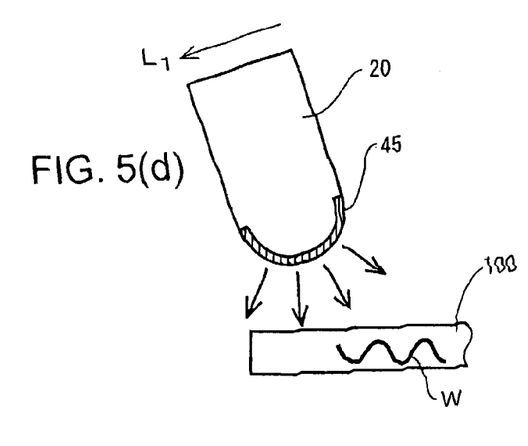

Moreover, a planer oscillator 41 may be employed in combination with a convex type acoustic lens 44 mounted to the emission surface of the transmitter 20 as shown in FIG. 5(c) or a convex type oscillator 45 may be provided for dispersing the ultrasonic wave from the transmitter 20 to have a plurality of the incident angle θ. In view of ensuring a desired level of the acoustic pressure, the focusing type probe is most favorable.

In this embodiment of the present invention described above, the two oscillators 40 of the transmitter 20 and the receiver 30 are identical to each other. However, the arrangements shown in FIGS. 2 and 5 may not be mandatory when the incident angle θ and the product FT remain uniform. Alternatively, either the transmitter 20 or the receiver 30 may be implemented by a conventional probe which can transmit and receive an ultrasonic wave along one direction.

Figure 6A:
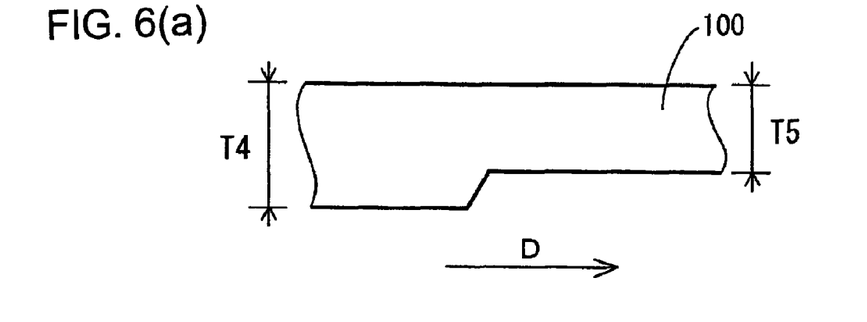
FIGS. 6(a) to 6(d) are cross sectional views of the test piece to be inspected according to the present invention.
Figure 6B:
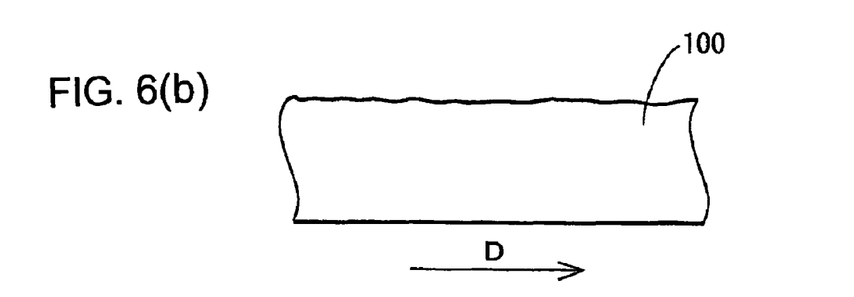
Figure 6C:
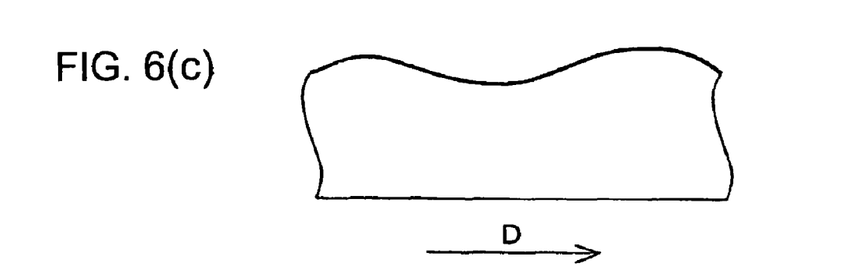
Figure 6D:
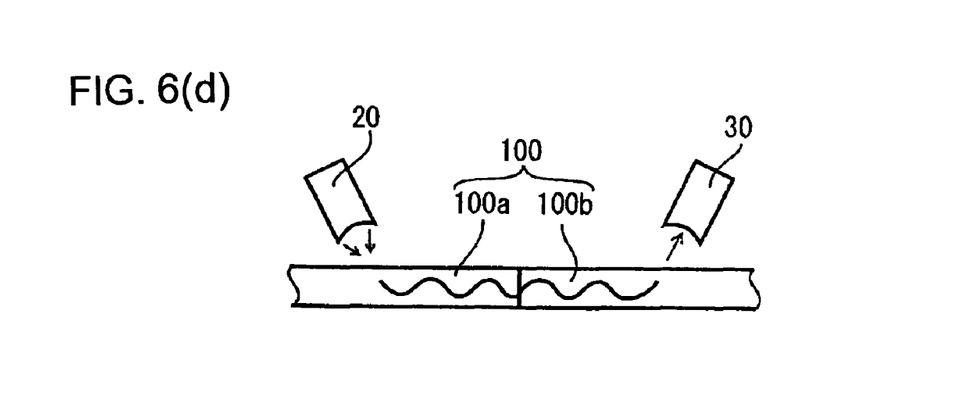

The present invention is applicable to not only a case where the thickness of the test piece 100 is monotonously varied. The plate wave can be generated with equal success not only when the thickness is varied simply from T4 to T5 with the scan head 10 being scanned in a direction D as shown in FIG. 6A but also when the incident angle θ is varied because of a rough surface of the test piece 100 as shown in FIG. 6B and when both the incident angle θ and the product FT are varied because the surface of the test piece 100 is undulated as shown in FIG. 6C. Furthermore, the transmission and reception of the ultrasonic wave is enabled through the test piece 100 which is made of different materials 100a, 100b bonded together across the propagating path of the ultrasonic wave as shown in FIG. 6D. Accordingly, a composite material such as a CFRP material for use in an aircraft which may be varied in both the thickness and the material properties can be inspected without difficulty. It would be understood that the present invention is applicable to an ultrasonic wave testing method of propagating the ultrasonic wave throughout not only the air but also any type of gas between a probe and a test piece through which its generating plate wave is propagated thus to test the test piece and an ultrasonic testing device using the method.

INDUSTRIAL APPLICABILITY

The present invention is applicable to an ultrasonic wave testing method for propagating an ultrasonic wave between a probe and a test piece, regardless of a transmitter and a receiver, for developing a plate wave thus to examine the test piece and to an ultrasonic testing device using the method. The test piece to be inspected by the testing device according to the present invention may be selected from a variety of materials since the testing device is of no-contact type using no medium. Particularly, it is favorable to inspect CFRP materials which are commonly used as aircraft structures.

What is claimed is:

1. An ultrasonic wave testing method comprising:
   preparing a ultrasonic testing device that transfers ultrasonic wave from an ultrasonic testing device to a test piece via a gas, the test piece transfers a propagating wave, the test piece is varied in a thickness of the test piece itself or a material or the thickness and the material,
   the ultrasonic testing device comprises:
   a probe assembly comprising a scan head:
   the scan head comprises a transmitter and a receiver that is disposed apart from the transmitter;
   the transmitter is a first focal point probe that focuses the ultrasonic wave at a plurality of different incident angles on a focal point via a gas, the focal point is on the test piece,
   the receiver is a second focal point probe that receives the ultrasonic wave propagated through the test piece via a gas at a plurality of different receivable angles;
   the method comprising the steps of:
   transmitting the ultrasonic wave from the transmitter at the different incident angles to the focal point on a normal region of the test piece via the gas;
   selecting a first incident angle of the incident angles from the different incident angles based on a product of a frequency of the ultrasonic wave and a thickness of the normal region according to a first material of the normal region first test area;
   generating a first propagating wave of a specific mode on the test piece based on a first ultrasonic wave that is transmitted from the transmitter at the first incident angle;
   propagating the first propagating wave through the test piece;
   selecting a first output angle of output angles from the different receivable angles based on a product of a frequency of the ultrasonic wave and a thickness of an output region of the test piece according to a material of the output region;
   receiving a released ultrasonic wave that is released from the output region at the first output angle by the receiver via the gas;
   generating a first signal based on the released and received ultrasonic wave; and
   detecting a defect in a propagating path of the first propagating wave based on the first signal.

2. An ultrasonic wave testing method according to claim 1, wherein the probe assembly is oriented so that a first rocking movement direction of the probe assembly intersects a direction of the propagating path.

3. An ultrasonic wave propagating method according to claim 2, wherein the focal point is located on and adjacent an outer surface of the test piece.

4. An ultrasonic wave propagating method according to claim 2, wherein the probe assembly is oriented so that a second movement direction of the probe assembly is in parallel with a direction of the propagating path.

5. An ultrasonic wave propagating method according to any of one claims 1 to 4, wherein the material of the test piece is a carbon fiber reinforced plastic (CFRP) material.

6. A ultrasonic testing device that is capable of transferring ultrasonic wave from an ultrasonic testing device to a test piece via a gas, the test piece transfers a propagating wave, the test peace has test areas that differ in thickness and materials, the ultrasonic testing device comprising:
 a probe assembly comprising a scan head:
  the scan head comprises a transmitter and a receiver that is disposed apart from the transmitter;
  the transmitter is a first focal point probe that focuses the ultrasonic wave at a plurality of different incident angles on a focal point via a gas, the focal point is on the test piece,
  the receiver is a second focal point probe that receives the ultrasonic wave propagated through the test piece via a gas at a plurality of receivable angles, the receiver receives the propagating wave transferred by the transmitter in the different incident angles and propagated through the test piece;
  the transmitter transmits the ultrasonic wave at the different incident angles to the focal point of each of the test areas via the gas;
  the transmitter is controlled to select a first incident angle of the incident angles from the different incident angles based on a product of a frequency of the ultrasonic wave and a thickness of a first test area of the test areas according to a first material of the first test area;
  the transmitter transmits a first ultrasonic wave at the first incident angle to generate a first propagating wave of a specific mode on the test piece based on the first ultrasonic wave to generate a first propagating wave of a specific mode on the test piece based on the first ultrasonic wave;
  the receiver receives the first ultrasonic wave propagated through the test piece via the gas, generates a first signal based on the received first ultrasonic wave, and detects a defect in a propagating path of the first propagating wave based on the first signal.

7. An ultrasonic testing device according to claim 6, wherein the probe assembly is oriented so that a first rocking movement direction of the probe assembly intersects a direction of the propagating path.

8. An ultrasonic testing device according to claim 7, wherein the focal point is located on and adjacent an outer surface of the test piece.

9. An ultrasonic testing device according to claim 7, wherein the probe assembly is oriented so that a second movement direction of the probe assembly is in parallel with a direction of the propagating path.

10. An ultrasonic testing device according to any of one claims 6 to 9, wherein the material of the test piece is a carbon fiber reinforced plastic (CFRP) material.

\* \* \* \* \*